United States Patent
Rivkin et al.

(10) Patent No.: US 8,685,972 B2
(45) Date of Patent: Apr. 1, 2014

(54) PYRIMIDINE DERIVATIVES FOR TREATMENT OF ALZHEIMER'S DISEASE

(75) Inventors: Alexey A. Rivkin, Boston, MA (US);
Sean P. Ahearn, Somerville, MA (US);
Stephanie M. Chichetti, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 269 days.

(21) Appl. No.: 13/058,231

(22) PCT Filed: Jul. 31, 2009

(86) PCT No.: PCT/US2009/052324
§ 371 (c)(1),
(2), (4) Date: May 5, 2011

(87) PCT Pub. No.: WO2010/019393
PCT Pub. Date: Feb. 18, 2010

(65) Prior Publication Data
US 2011/0207733 A1   Aug. 25, 2011

Related U.S. Application Data

(60) Provisional application No. 61/188,832, filed on Aug. 13, 2008.

(51) Int. Cl.
*C07D 401/14* (2006.01)
*A61K 31/505* (2006.01)

(52) U.S. Cl.
USPC ........ 514/235.8; 514/269; 514/275; 544/122; 544/298; 544/324

(58) Field of Classification Search
USPC ........ 544/122, 298, 324; 514/235.8, 269, 275
See application file for complete search history.

(56) References Cited

U.S. PATENT DOCUMENTS

| | | | |
|---|---|---|---|
| 5,922,706 A * | 7/1999 | Dorn et al. ................. | 514/227.5 |
| 7,166,599 B2 | 1/2007 | Bornemann et al. | |
| 2002/0040031 A1 | 4/2002 | Glasky et al. | |
| 2010/0041680 A1 | 2/2010 | Rivkin | |
| 2010/0204230 A1 | 8/2010 | Blurton et al. | |

FOREIGN PATENT DOCUMENTS

| WO | WO 02/060392 | * | 8/2002 |
|---|---|---|---|
| WO | 2010019392 | | 2/2010 |

OTHER PUBLICATIONS

Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Zlokovic, New Therapeutic Targets in the Neurovascular Pathway in Alzheimer's Disease, Neurotherapeutics, vol. 5, pp. 409-414, Jul. 2008.*
Oh et al., Maximizing the Potential of Plasma Amyloid-Beta as a Diagnostic Biomarker for Alzheimer's Disease, Neuromol Med (2008) 10:195-207.*

* cited by examiner

*Primary Examiner* — Deepak Rao
(74) *Attorney, Agent, or Firm* — Susan L. Hess; John C. Todaro

(57) ABSTRACT

The invention encompasses pyrimidine derivatives as gamma secretase modulators, useful for treating diseases associated with the deposition of beta-amyloid peptide in the brain, such as Alzheimer's disease, or of preventing or delaying the onset of dementia associated with such diseases. Pharmaceutical compositions and methods of use are included.

6 Claims, No Drawings

PYRIMIDINE DERIVATIVES FOR TREATMENT OF ALZHEIMER'S DISEASE

This invention relates to compounds for use in therapeutic treatment of the human body. In particular, it provides compounds useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS*, 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science*, 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature*, 423 (2003), 435-9). Other proposed methods of treatment include administering a compound which blocks the aggregation of Aβ, and administering an antibody which selectively binds to Aβ.

However, recent reports (Pearson and Peers, *J. Physiol.*, 575.1 (2006), 5-10) suggest that Aβ may exert important physiological effects independent of its role in AD, implying that blocking its production may lead to undesirable side effects. Furthermore, γ-secretase is known to act on several different substrates apart from APP (e.g. notch), and so inhibition thereof may also lead to unwanted side effects. There is therefore an interest in methods of treating AD that do not suppress completely the production of Aβ, and do not inhibit the action of γ-secretase.

One such proposed treatment involves modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and U.S. 2002/0128319 and Weggen et al *Nature*, 414 (2001) 212-16; Morihara et al, *J. Neurochem.*, 83 (2002), 1009-12; and Takahashi et al, *J. Biol. Chem.*, 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J. Neuroscience*, 22 (2002), 226-54). U.S. 2002/0015941 teaches that agents which potentiate capacitative calcium entry activity can lower Aβ(1-42).

Further classes of compounds capable of selectively attenuating Aβ(1-42) production are disclosed on WO 2005/054193, WO 2005/013985, WO 2006/008558, WO 2005/108362 and WO 2006/043064.

WO 2004/110350 discloses a variety of polycyclic compounds as suitable for modulating Aβ levels, but neither discloses nor suggests the compounds described herein.

According to the invention, there is provided a compound of formula I:

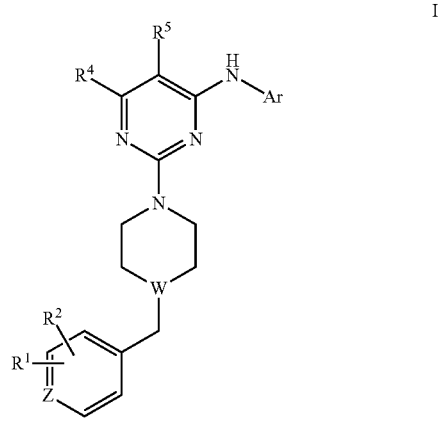

or a pharmaceutically acceptable salt or hydrate thereof, wherein:

W represents CH or N;

Z represents N or CR$^3$;

R$^1$, R$^2$, and R$^3$ independently represent H, C$_{1-4}$alkyl, C$_{1-4}$alkoxy, halogen or CF$_3$;

R$^4$ and R$^5$ independently represent H or (CH$_2$)$_m$—X, where m is 0 or 1 and X represents halogen, 5- or 6-membered heteroaryl which is optionally substituted with up to 2 C$_{1-4}$alkyl groups, CN, CF$_3$, R$^6$, OR$^6$, N(R$^6$)$_2$, SO$_2$R$^6$, CO$_2$R$^6$ or CON(R$^6$)$_2$ where each R$^6$ independently represents H, phenyl, C$_{1-4}$alkyl or hydroxyC$_{1-4}$alkyl or two R$^6$ groups attached to the same nitrogen optionally complete an N-heterocycle; or R$^4$ and R$^5$ together may complete a fused 5- or 6-membered carbocyclic or heterocyclic ring; and Ar represents a phenyl or 5- or 6-membered heteroaryl ring bearing from 2 to 4 substituents selected from:
 (a) C$_{1-6}$alkyl;
 (b) C$_{3-6}$cycloalkyl;
 (d) C$_{3-6}$cycloalkylC$_{1-6}$alkyl;
 (e) C$_{2-6}$alkenyl;
 (f) OR$^7$;
 (g) CO$_2$R$^7$;

(h) N(R$^7$)$_2$
(i) SR$^7$; and
(j) CF$_3$;
where each R$^7$ represents C$_{1-6}$alkyl.

Where a variable occurs more than once in formula I, the identity taken by said variable at any particular occurrence is independent of the identity taken at any other occurrence.

As used herein, the expression "C$_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "C$_{2-6}$alkenyl", "hydroxyC$_{1-6}$alkyl", "heteroarylC$_{1-6}$alkyl", "C$_{2-6}$alkynyl" and "C$_{1-6}$alkoxy" are to be construed in an analogous manner.

The expression "C$_{3-6}$cycloalkyl" refers to cyclic non-aromatic hydrocarbon groups containing from 3 to 6 ring carbon atoms. Examples include cyclopropyl, cyclobutyl, cyclopentenyl, cyclopentyl and cyclohexyl.

The term "heterocyclic" refers to mono- or bicyclic ring systems in which at least one ring atom is selected from N, O and S. Unless indicated otherwise, the term includes both saturated and unsaturated systems, including aromatic systems. Heterocyclic groups may be bonded via a ring carbon or a ring nitrogen, unless otherwise indicated. "Heteroaryl" refers to heterocyclic groups that are aromatic.

The term "halogen" as used herein includes fluorine, chlorine, bromine and iodine, of which fluorine and chlorine are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of a carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the stereoisomeric forms encompassed by formula I, both optical and geometrical, fall within the scope of the invention, singly or as mixtures in any proportion.

In formula I, W represents CH or N. In a particular embodiment W represents CH.

Z represents N or CR$^3$. In a particular embodiment Z is N.

Preferably, at least one of R$^1$ and R$^2$ is H, and in a particular embodiment R$^1$=R$^2$=H.

R$^3$ (when present) is very suitably H or C$_{1-4}$alkoxy (eg. methoxy).

In one embodiment, R$^4$ and R$^5$ independently represent H or (CH$_2$)$_m$—X, where m is 0 or 1 and X represents halogen, 5- or 6-membered heteroaryl (which optionally bears up to 2 C$_{1-4}$alkyl substituents), CN, CF$_3$, R$^6$, OR$^6$, N(R$^6$)$_2$, SO$_2$R$^6$, CO$_2$R$^6$ or CON(R$^6$)$_2$ where each R$^6$ independently represents H, phenyl, C$_{1-4}$alkyl or hydroxyC$_{1-4}$alkyl, or two R$^6$ groups attached to the same nitrogen optionally complete an N-heterocyclyl group (e.g. azetidine, pyrrolidine, piperidine or morpholine). When m=1, X very suitably represents OR$^6$ or SO$_2$R$^6$, e.g. OH or SO$_2$Me. When X represents a heteroaryl group, said heteroaryl group is very suitably pyridyl or is 5-membered, such as oxadiazole, pyrazole or imidazole. Examples of groups suitably represented by R$^4$ and/or R$^5$ include H, Halogen (especially F, Cl or Br), CN, CF$_3$, C$_{1-4}$alkyl, phenyl, C$_{1-4}$alkoxy, CONR$^6$$_2$, NR$^6$$_2$, CO$_2$H, CO$_2$Me, SO$_2$Me, hydroxymethyl, CH$_2$SO$_2$Me, 2-hydroxy-2-propyl, 1-hydroxyethyl, pyridyl, 1-methylpyrazol-4-yl and 1,3,4-oxadiazol-2-yl. Specific examples of groups represented by R$^4$ and/or R$^5$ include H, F, Cl, methoxy, dimethylamino, diethylamino, pyrrolidin-1-yl, morpholin-4-yl, methyl, CO$_2$Me, CH$_2$OH, 3-pyridyl and 1-methylpyrazol-4-yl.

Alternatively, R$^4$ and R$^5$ together may complete a fused 5- or 6-membered carbocyclic or heterocyclic ring. Examples of suitable fused rings include cyclopentane, phenyl, thiopyran and pyridine.

In a particular embodiment, at least one of R$^4$ and R$^5$ is H.

Ar represents a phenyl or 5- or 6-membered heteroaryl ring bearing from 2 to 4 substituents as defined previously. Heteroaryl rings represented by Ar are very suitably nitrogen-containing rings such as pyridine, pyrazole, imidazole or triazole. In a particular embodiment, Ar represents substituted phenyl or pyrazol-5-yl.

When Ar represents substituted phenyl, Ar preferably bears 2 or 3 substituents. When Ar represents 5- or 6-membered heteroaryl, Ar preferably bears 2 substituents. Regardless of the identity of Ar, preferably at least one of the substituents is C$_{1-6}$alkyl, and preferably not more than one substituent is other than C$_{1-6}$alkyl. In one embodiment, Ar bears a C$_{1-6}$alkyl substituent on the ring position adjacent to the point of attachment of Ar to the remainder of the molecule. Specific examples of substituents borne by Ar include:

C$_{1-6}$alkyl, such as methyl, ethyl, isopropyl, n-butyl and t-butyl;

OR$^7$ where R$^7$ represents C$_{1-6}$alkyl, in particular C$_{1-4}$alkyl, such as methoxy, ethoxy and isopropoxy;

CO$_2$R$^7$ where R$^7$ represents C$_{1-6}$alkyl, in particular C$_{1-4}$alkyl, such as CO$_2$Me;

and N(R$^7$)$_2$ where R$^7$ represents C$_{1-6}$alkyl, in particular C$_{1-4}$alkyl, such as dimethylamino and diethylamino.

Therefore, in a subset of the compounds of formula I Ar represents:

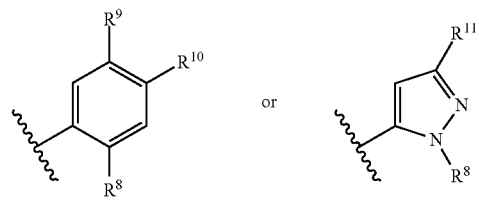

where R$^8$ represents C$_{1-6}$alkyl; and R$^9$, R$^{10}$ and R$^{11}$ independently represent:

H;
C$_{1-6}$alkyl;
OR$^7$ where R$^7$ represents C$_{1-6}$alkyl;
CO$_2$R$^7$ where R$^7$ represents C$_{1-6}$alkyl; or
N(R$^7$)$_2$ where R$^7$ represents C$_{1-6}$alkyl;
with the proviso that at least one of R$^9$ and R$^{10}$ is other than H and that R$^{11}$ is other than H.

Within this subset, suitable identities for Ar include 4-ethoxy-5-isopropyl-2-methylphenyl, 5-t-butyl-2-methylphenyl, 5-dimethylamino-2-methylphenyl, and 5-isopropoxy-2-methylphenyl.

Another subset of the compounds of the invention consists of the compounds of formula II:

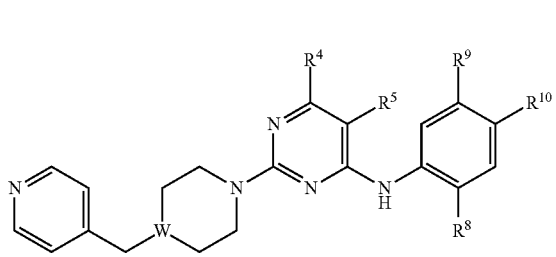

and pharmaceutically acceptable salts and hydrates thereof; wherein W, $R^4$, $R^5$, $R^8$, $R^9$ and $R^{10}$ have the same definitions and specific identities as before. In a sub-embodiment W represents CH.

Specific examples of compounds of the invention are disclosed in the Examples later herein.

Compounds of formula I may be prepared by reaction of piperidine derivatives (1) with halides (2):

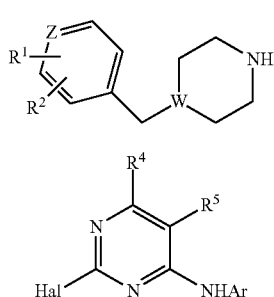

where Hal represents Cl, Br or I and $R^1$, $R^2$, W, Z and Ar have the same meanings as before. The reaction takes place in an alkanol solvent (e.g. isopropanol) with microwave heating (e.g. at about 160° C.) in the presence of a tertiary amine (e.g. diisopropylethylamine). Alternatively, the reaction may be carried out under Buchwald conditions, i.e. with heating in a solvent such as toluene or dioxan in the presence of base (such as sodium carbonate) and Pd(0) and phosphine catalysts. Suitable catalysts include tris(dibenzylideneacetone)dipalladium(0) and 4,5-bis(diphenylphosphino)-9,9-dimethylxanthene.

Compounds (2) may be prepared similarly by treatment of dihalides (3) with Ar—$NH_2$:

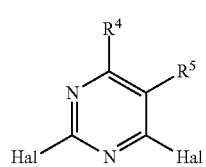

where Hal, $R^4$, $R^5$ and Ar have the same meanings as before. The reaction may be carried out by heating (e.g. in the range 80-120° C.) in the presence of a tertiary amine (e.g. triethylamine or diisopropylethylamine), either neat or in an alkanol solvent such as ethanol.

It will be apparent to those skilled in the art that the conventional techniques of organic synthesis may be used to convert individual compounds in accordance with formula I into other compounds also in accordance with formula I. Such techniques include ester or amide formation or hydrolysis, oxidation, reduction, alkylation and carbon-carbon bond formation via coupling or condensation. Such techniques may similarly be applied to the synthetic precursors of compounds of formula I.

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3$^{rd}$ ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt or hydrate thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt or hydrate thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt or hydrate thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt or hydrate thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), polyvinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, U.S. 2002/0025955 and U.S.2002/0022621, and also including GSK-3 inhibitors, particularly GSK-3α inhibitors, such as lithium, as disclosed in Phiel et al, *Nature,* 423 (2003), 435-9.

Alternatively, the amyloid modifier may be a compound which inhibits the aggregation of Aβ or otherwise attenuates is neurotoxicicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in U.S. 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

EXAMPLES

The ability of the compounds of Formula I to selectively inhibit production of Aβ(1-42) may be determined using the following assay:

Cell-Based γ-Secretase Assay

Human SH-SY5Y neuroblastoma cells overexpressing the direct β-secretase substrate SPA4CT were induced with sodium butyrate (10 mM) for 4 hours prior to plating. Cells were plated at 35,000 cells/well/100 µl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 µl of these diluted compounds in $Me_2SO$ were further diluted into 182 µl dilution buffer (phenol red-free MEM/10% FBS, 50 mM HEPES, 1% Glutamine) and 10 µl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 25 µl and 50 µl media were transferred into a standard Meso avidin-coated 96-well plate for detection of Aβ(40) and Aβ(42) peptides, respectively. 25 µl Meso Assay buffer (PBS, 2% BSA, 0.2% Tween-20) was added to the Aβ(40) wells followed by the addition of 25 µl of the respective antibody premixes to the wells:

Aβ(40) premix: 1 µg/ml ruthenylated G2-10 antibody, 4 µg/ml biotinylated 4G8 antibody diluted in Origen buffer Aβ(42) premix: 1 µg/ml ruthenylated G2-11 antibody, 4 µg/ml biotinylated 4G8 antibody diluted in Origen buffer (Biotinylated 4G8 antibody supplied by Signet Pathology Ltd; G2-10 and G2-11 antibodies supplied by Chemicon)

After overnight incubation of the assay plates on a shaker at 4° C., the Meso Scale Sector 6000 Imager was calibrated according to the manufacturer's instructions. After washing the plates 3 times with 150 µl of PBS per well, 150 µl Meso Scale Discovery read buffer was added to each well and the plates were read on the Sector 6000 Imager according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 µl of 10×MTS/PES was added to the remaining 50 µl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for Aβ(1-42) inhibition of less than 5 µM and in most cases less than 1.0 µM. Furthermore, said values were typically at least 2-fold lower than the corresponding $IC_{50}$ values for Aβ(1-40) inhibition, more typically at least 5-fold lower.

Representative $IC_{50}$ values for Aβ(1-42) inhibition obtained for compounds exemplified below were in the following ranges:

1.5-3.0 µM—Examples 6, 10, 22

0.5-1.5 µM—Examples 4, 11, 12, 18

<0.5 µM—all other examples.

Assay for in vivo Efficacy

APP-YAC transgenic mice (20-30 g; 2-6 months old) and Sprague Dawley rats (200-250 g; 8-10 weeks old) were kept on 12-hr light/dark cycle with unrestricted access to food and water. Mice and rats were fasted overnight and were then dosed orally at 10 ml/kg with test compound formulated in either imwitor:Tween-80 (50:50) or 10% Tween-80, respectively. For compound screening studies, test compounds were administered at a single dose (20 or 100 mg/kg) and blood was taken serially at 1 and 4 hrs via tail bleed from mice and terminally at 7 hrs for mice and rats via cardiac puncture. In dose response studies, compounds were given at 0.1, 3, 10, 30, and 100 mg/kg and blood was taken terminally at 7 hrs from mice and rats via cardiac puncture. Following euthanasia by $CO_2$, forebrain tissue was harvested from animals and stored at −80 degrees. For PD analysis of brain Aβ levels, soluble Aβ was extracted from hemi-forebrains by homogenization in 10 volumes of 0.2% DEA in 50 mM NaCl followed by ultracentrifugation. Levels of Aβ 42/40 were analyzed using Meso Scale technology (electrochemiluminescence) with biotinylated 4G8 capture antibody and ruthenium labeled 12F4 or G210 detection antibodies for Aβ 42 and Aβ 40, respectively. For PK analysis, blood and brain samples were processed using a protein precipitation procedure with the remaining filtrate being analyzed via LC/MS/MS to determine drug exposure levels, brain penetration, and ED50/EC50, where appropriate.

Example 1

N-(5-tert-butyl-2-methylphenyl)-5-methoxy-2-[4-(pyridin-4-ylmethyl)piperidin-1-yl]pyrimidin-4-amine

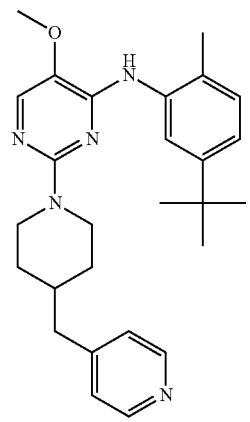 [SMILES: COc1cnc(N2CCC(Cc3ccncc3)CC2)nc1Nc1cc(C(C)(C)C)ccc1C]

Step 1: N-(5-tert-butyl-2-methylphenyl)-2-chloro-5-methoxypyrimidin-4-amine

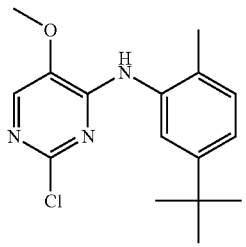 [SMILES: COc1cnc(Cl)nc1Nc1cc(C(C)(C)C)ccc1C]

A solution of 2,4-dichloro-5-methoxypyrimidine (200 mg, 1.12 mmol), 2-methyl-5-t-butylaniline (192 mg, 1.17 mmol) and diisopropylethylamine (1.5 mL) in 2-propanol (1.5 mL) was heated at 120° C. for 17 h in an oil bath. The mixture was cooled to room temperature and solvent was evaporated under reduced pressure. The residue was purified by column chromatography on silica gel (Biotage system, EtOAc/Hexane, 0%-100%) to afford the product as a solid (166 mg, 48.6%).

Step 2: N-5-tert-butyl-2-methylphenyl)-5-methoxy-2-[4-(pyridin-4-ylmethyl)piperidin-1-yl]pyrimidin-4-amine A solution of the product of Step 1 (166 mg, 0.543 mmol), 4-piperidin-4-ylmethylpyridine dihydrochloride (162 mg, 0.651 mmol) and diisopropylethylamine (1.5 mL) was irradiated in 2-propanol (1.5 mL), in a microwave oven, at 180° C. for 2.5 hrs. The mixture was cooled and the solvent was evaporated under reduced pressure. The residue was purified by column chromatography on silica gel (Biotage system, MeOH/dichloromethane, 0%-15%) to give the product (165 mg, 68.2%) as a solid. $^1$H-NMR (600 MHz, CDCl$_3$) δ=1.21 (2H, m), 1.28 (9H, s), 1.60 (2H, d, J=13.19), 1.74 (1H, m), 2.23 (3H, s), 2.49 (2H, d, J=7.35), 2.72 (2H, td, J=12.76, 1.51), 3.80 (3H, s), 4.64 (2H, d, J=13.35), 6.96 (1H, s), 6.99 (1H, dd, J=7.88, 1.9), 7.03 (2H, d, J=5.43), 7.08 (1H, d, J=8.15), 7.60 (1H, s), 8.27 (1H, d, J=1.9), 8.44 (2H, d, J=5.7), LC-ESMS observed [M+H]+ 446.2 (calcd 446.6).

Examples 2-22

The following were prepared by the same procedure, using the appropriate aniline derivative and dichloropyrimidine derivative in Step 1:

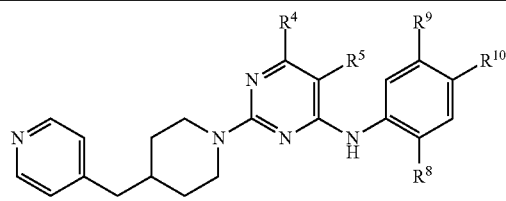

| Example | R$^4$ | R$^5$ | R$^8$ | R$^9$ | R$^{10}$ |
|---|---|---|---|---|---|
| 2 | H | H | Me | Isopropyl | OEt |
| 3 | H | F | Me | Isopropyl | OEt |
| 4 | H | H | Me | t-butyl | H |

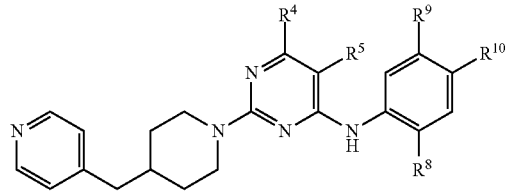

| Example | R$^4$ | R$^5$ | R$^8$ | R$^9$ | R$^{10}$ |
|---|---|---|---|---|---|
| 5 | H | OMe | Me | Isopropyl | OEt |
| 6 | H | OMe | Me | NMe$_2$ | H |
| 7 | H | NMe$_2$ | Me | Isopropyl | OEt |
| 8 | H | Pyrrolidinyl | Me | Isopropyl | OEt |
| 9 | H | Me | Me | Isopropyl | OEt |
| 10 | H | H | Me | NMe$_2$ | Me |
| 11 | H | Cl | Me | Isopropyl | OEt |
| 12 | H | H | Me | Isopropoxy | H |
| 13 | Me | H | Me | Isopropyl | OEt |
| 14 | NEt$_2$ | H | Me | Isopropyl | OEt |
| 15 | Morpholinyl | H | Me | Isopropyl | OEt |
| 16 | CO$_2$Me | H | Me | Isopropyl | OEt |
| 17 | Cl | H | Me | t-butyl | H |
| 18 | CO$_2$Me | H | Me | t-butyl | H |
| 19 | CH$_2$OH | H | Me | t-butyl | H |
| 20 | 3-pyridyl | H | Me | t-butyl | H |
| 21 | 1-Me-pyrazol-4-yl | H | Me | t-butyl | H |
| 22 | H | F | Me | t-butyl | H |

The invention claimed is:

1. A compound of formula I:

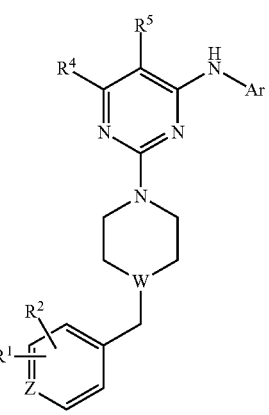

or a pharmaceutically acceptable salt or hydrate thereof, wherein:
W represents CH;
Z represents N;
R$^1$ and R$^2$ independently represent H, C$_{1-4}$alkyl, C$_{1-4}$alkoxy, halogen or CF$_3$;
R$^4$ and R$^5$ independently represent H or (CH$_2$)$_m$—X, where m is 0 or 1 and X represents halogen, 5- or 6-membered heteroaryl which is optionally substituted with up to 2 C$_{1-4}$alkyl groups, CN, CF$_3$, R$^6$, OR$^6$, N(R$^6$)$_2$, SO$_2$R$^6$, CO$_2$R$^6$ or CON(R$^6$)$_2$ where each R$^6$ independently represents H, phenyl, C$_{1-4}$alkyl or hydroxyC$_{1-4}$alkyl or two R$^6$ groups attached to the same nitrogen optionally complete an N-heterocycle; and
Ar represents a phenyl or 5- or 6-membered heteroaryl ring bearing from 2 to 4 substituents selected from:
(a) C$_{1-6}$alkyl;

(b) $C_{3-6}$cycloalkyl;
(d) $C_{3-6}$cycloalkyl $C_{1-6}$alkyl;
(e) $C_{2-6}$alkenyl;
(f) $OR^7$;
(g) $CO_2R^7$;
(h) $N(R^7)_2$
(i) $SR^7$; and
(j) $CF_3$;
where each $R^7$ represents $C_{1-6}$ alkyl.

2. A compound according to claim 1 or a pharmaceutically acceptable salt or hydrate thereof, wherein Ar represents:

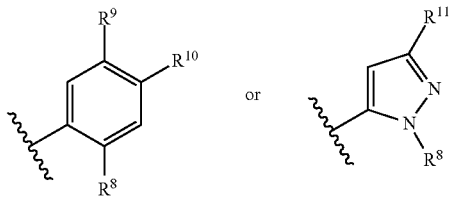

where $R^8$ represents $C_{1-6}$alkyl; and $R^9$, $R^{10}$ and $R^{11}$ independently represent:
H;
$C_{1-6}$ alkyl;
$OR^7$ where $R^7$ represents $C_{1-6}$ alkyl;
$CO_2R^7$ where $R^7$ represents $C_{1-6}$ alkyl; or
$N(R^7)_2$ where $R^7$ represents $C_{1-6}$alkyl;

with the proviso that at least one of $R^9$ and $R^{10}$ is other than H and that $R^{11}$ is other than H.

3. A compound according to claim 2 of formula II:

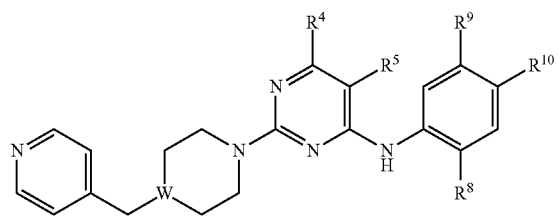

or a pharmaceutically acceptable salt or hydrate thereof.

4. A compound according to claim 3 or a pharmaceutically acceptable salt or hydrate thereof, wherein at least one of $R^4$ and $R^5$ is H.

5. A pharmaceutical composition comprising a compound according to claim 1 or a pharmaceutically acceptable salt or hydrate thereof, and a pharmaceutically acceptable carrier.

6. A method of treating Alzheimer's disease, which comprises administering to a patient in need thereof a therapeutically effective amount of a compound according to claim 1 or a pharmaceutically acceptable salt or hydrate thereof.

* * * * *